United States Patent
Mayeaux (10) Patent No.: US 8,904,886 B1
(45) Date of Patent: Dec. 9, 2014

(54) DEVICES FOR OBTAINING CYLINDER SAMPLES OF NATURAL GAS OR PROCESS GAS AND METHODS THEREFORE

(75) Inventor: Donald P Mayeaux, Gonzales, LA (US)

(73) Assignee: A+ Manufacturing LLC, Gonzales, LA (US)

( * ) Notice: Subject to any disclaimer, the term of this patent is extended or adjusted under 35 U.S.C. 154(b) by 772 days.

(21) Appl. No.: 12/968,017

(22) Filed: Dec. 14, 2010

Related U.S. Application Data (60) Continuation-in-part of application No. 12/344,118, filed on Dec. 26, 2008, now Pat. No. 7,874,221, which (Continued)

(51) Int. Cl.
*G01N 1/22* (2006.01)
*G01N 1/20* (2006.01)
*G01N 1/10* (2006.01)

(52) U.S. Cl.
CPC ...... *G01N 1/2247* (2013.01); *G01N 2001/2238* (2013.01); *G01N 2001/105* (2013.01)
USPC ..................... 73/864.51; 73/864.91

(58) Field of Classification Search
CPC .......... G01N 1/2247; G01N 2001/105; G01N 2001/2238
USPC ............... 73/863.52, 863.81, 864.51–864.52, 73/864.63, 864.91
See application file for complete search history.

(56) References Cited

U.S. PATENT DOCUMENTS

| 3,203,247 A | 8/1965 | Bicek .......................... 73/864.91 |
| 3,273,647 A | 9/1966 | Briggs, Jr. et al. ............ 166/100 |

(Continued)

FOREIGN PATENT DOCUMENTS

| DE | 3310032 A1 | 9/1984 | ............... G01N 1/12 |
| JP | 6-288880 | 10/1994 | ...................... 73/863 |

(Continued)

OTHER PUBLICATIONS

Manual of Petro Meas Stde Ch 14, Sec 1, Collecting and Handling of Natural Gas Samples for Custody Transfer, API (4th Ed, Aug. 1993), pp. 2, 3, 6, and 12.

(Continued)

*Primary Examiner* — Thomas P Noland
(74) *Attorney, Agent, or Firm* — Joseph T Regard, Ltd plc (57) ABSTRACT

A moveable end (ME) sample cylinder device is provided which employs a method of collection wherein the initial cylinder volume of the collection vessel or sampling cylinder is zero. The sample cylinder is inserted into the pressurized gas (or fluid) source for spot sampling thereof, said sample cylinder employing a piston or moveable end configured such that purging of the cylinder sample cavity is not required, since the sample cavity volume is essentially eliminated prior to sampling by the location of the piston within the cavity, the cavity expanding upon sampling via piston movement within the cavity. Also contemplated is a cap/body (CB) spot sample cylinder having a low internal volume and which can be inserted into a pressurized process through common valving. Insertion of the CB sample cylinder into the process eliminates purging of interconnecting tubing and also eliminates the impact of low ambient temperatures which can otherwise alter the spot sample composition. The CB sample cylinder cap may be provided to function as a fill/empty valve.

10 Claims, 10 Drawing Sheets

Related U.S. Application Data is a division of application No. 11/151,018, filed on Jun. 13, 2005, now Pat. No. 7,481,125, which is a continuation-in-part of application No. 10/631,501, filed on Jul. 31, 2003, now Pat. No. 7,225,690, and a continuation-in-part of application No. 10/408,026, filed on Apr. 3, 2003, now Pat. No. 6,904,816, which is a division of application No. 09/915,192, filed on Jul. 25, 2001, now Pat. No. 6,701,794, which is a continuation-in-part of application No. 09/162,239, filed on Sep. 28, 1998, now Pat. No. 6,357,304, which is a continuation-in-part of application No. 08/701,406, filed on Aug. 22, 1996, now Pat. No. 5,841,036.

(60) Provisional application No. 60/646,314, filed on Jan. 24, 2005, provisional application No. 60/100,736, filed on Aug. 2, 2002, provisional application No. 60/221,335, filed on Jul. 26, 2000.

(56) References Cited

U.S. PATENT DOCUMENTS

| | | | | |
|---|---|---|---|---|
| 3,638,499 | A * | 2/1972 | Saint-Andre | G01N 2001/105 |
| 3,831,953 | A | 8/1974 | Leibfritz et al. | 277/637 |
| 3,835,710 | A | 9/1974 | Pogorski | 73/864.74 |
| 3,848,579 | A | 11/1974 | Villa-Real | 600/577 |
| 3,872,721 | A | 3/1975 | Ilfrey | 73/152.28 |
| 4,014,216 | A | 3/1977 | Thornton et al. | 73/863.23 |
| 4,112,768 | A | 9/1978 | Holland et al. | 75/863.24 |
| 4,157,040 | A | 6/1979 | Barton et al. | 73/863.23 |
| 4,175,424 | A * | 11/1979 | Bimond et al. | 73/864.91 X |
| 4,269,064 | A | 5/1981 | Johnson et al. | 73/863.84 X |
| 4,346,613 | A * | 8/1982 | Turner et al. | 73/864.51 |
| 4,402,911 | A * | 9/1983 | Walters | 73/864.51 X |
| 4,459,266 | A * | 7/1984 | Lamoreaux | G01N 2001/2238 |
| 4,628,750 | A | 12/1986 | Welker | 73/863.71 X |
| 4,800,763 | A | 1/1989 | Hakkers et al. | 73/863 |
| 4,821,585 | A | 4/1989 | Kempe | 73/863.23 |
| 4,865,729 | A * | 9/1989 | Saxena et al. | 210/198.2 |
| 4,865,811 | A | 9/1989 | Newton et al. | 422/81 |
| 4,928,541 | A | 5/1990 | Toon et al. | 73/864.63 |
| 4,974,456 | A | 12/1990 | Ortiz et al. | 73/863.52 |
| 5,191,801 | A | 3/1993 | Allen et al. | 73/864.34 |
| 5,205,988 | A | 4/1993 | Tanaka et al. | 422/91 |
| 5,303,599 | A | 4/1994 | Welker | 73/863.84 |
| 5,369,034 | A * | 11/1994 | Hargett et al. | 436/155 |
| 5,406,855 | A | 4/1995 | Welker | 73/863.83 |
| 5,442,969 | A | 8/1995 | Troutner et al. | 73/863.71 |
| 5,536,474 | A | 7/1996 | Ungerer et al. | 73/864.62 X |
| 5,637,792 | A | 6/1997 | Kimura et al. | 73/116 |
| 5,677,478 | A * | 10/1997 | Murphy, Jr. | 73/38 |
| 5,794,695 | A | 8/1998 | Peterson | 166/264 |
| 5,814,741 | A | 9/1998 | Wang et al. | 73/863.12 |
| 5,844,123 | A | 12/1998 | Marsh et al. | 73/863.12 X |
| 5,899,349 | A * | 5/1999 | Moore | 215/277 |
| 6,021,661 | A * | 2/2000 | Lowell et al. | 73/38 |
| 6,354,345 | B1 | 3/2002 | Nabity et al. | 141/284 |
| 6,405,580 | B2 | 6/2002 | Kirts et al. | 73/60.11 |
| 6,539,312 | B1 | 3/2003 | Nimberger et al. | 73/863.84 X |
| 6,659,177 | B2 | 12/2003 | Bolze et al. | 166/264 |
| 6,675,664 | B1 | 1/2004 | Lilienthal et al. | 73/863.23 |
| 6,793,819 | B2 | 9/2004 | Glenwright et al. | 73/863.84 X |
| RE39,457 | E | 1/2007 | Guirguis | 435/7.2 |
| 7,178,415 | B2 * | 2/2007 | Britt | 73/864.67 |
| 7,552,648 | B2 * | 6/2009 | McMechan et al. | 73/803 |
| 8,556,826 | B2 * | 10/2013 | Wan et al. | 73/864.91 X |
| 2003/0033858 | A1 | 2/2003 | Lambert et al. | 73/53.01 |
| 2003/0051565 | A1 | 3/2003 | Nimberger | 73/864.34 |
| 2003/0089526 | A1 | 5/2003 | Beeker | 175/58 |
| 2003/0103551 | A1 | 6/2003 | Haddad et al. | 374/136 |

FOREIGN PATENT DOCUMENTS

| | | | | |
|---|---|---|---|---|
| SU | 1250251 | A | 8/1986 | A61B 5/08 |
| SU | 1520382 | A | 11/1989 | G01N 1/22 |
| WO | 95/02176 | | 1/1995 | G01N 1/00 |

OTHER PUBLICATIONS

Technical Memorandum—Metering Research Facility Program; Gas Research Institute, Transmission Operations, Apr. 1998, pp. 32-33.
The Calibration Station (Newsletter of Colorado Engineering Experiment Station, Inc.) vol. 1, Fall Winter 1997, pp. 1-2.
Welker, Thomas F., Sample Conditioning, 1997 Proceedings of AM SCH of Gas Measurement Tech, pp. 79-81.
Ting, V.C., Effect of Entrained Liquid on Orifice Measurement, Sep. 1998, Proceedings of AM Sch of Gas Measurement Tech, pp. 85-88.
A+ Corp, Prairieville, LA Series 100 Genie Membrane Separators Brochure, Rev Aug. 1998, pp. 1-7.
A+ Corp, Prairieville, LA Series 200 Genie Membrane Separators Brochure, Rev Mar. 1996, pp. 1-6.
A+ Corporation, "Series 100 Genie Membrane Separators", Aug. 1998, pp. 1-7.
NB9103334, Discrete Depth Groundwater Sampler, Sample Container and Monitor. Mar. 1, 1991, IBM Technical Disclosure Bulletin, Volume No. 33, Issue No. 10B, Page No. 334-335.

* cited by examiner

DEVICES FOR OBTAINING CYLINDER SAMPLES OF NATURAL GAS OR PROCESS GAS AND METHODS THEREFORE

DOMESTIC PRIORITY DATA AS CLAIMED BY APPLICANT

The present application is continuation in part of U.S. patent application Ser. No. 12/344,418 filed Dec. 26, 2008 entitled "Devices for Obtaining Cylinder Samples of Natural Gas or Process A Gas, and Methods Therefore", which Ser. No. 12/344,418 application is a divisional of U.S. patent application Ser. No. 11/151,018, U.S. Pat. No. 7,481,125, filed Jun. 13, 2005, which claims the benefit of Provisional Application 60/646,314 filed Jan. 24, 2005 entitled "Devices for Obtaining Cylinder Samples of Natural Gas or Process Gas"; which Ser. No. 11/151,018 application is also a continuation in part of U.S. patent application Ser. No. 10/631,501, U.S. Pat. No. 7,225,690 filed Jul. 31, 2003, entitled "Multi-Cavity Sample Cylinder with Integrated Valving", which Ser. No. 10/631,501 application claims the benefit of Provisional Application 60/400,736 having a filing date of Aug. 2, 2002; which Ser. No. 11/151,018 application is also a continuation in part of U.S. patent application Ser. No. 10/408,026, U.S. Pat. No. 6,904,816, which is a divisional of U.S. patent application Ser. No. 09/915,192, U.S. Pat. No. 6,701,794 filed Jul. 25, 2001, which claims the benefit of Provisional Application 60/221,335 filed Jul. 26, 2000, and is a continuation in part of Ser. No. 09/162,239 now U.S. Pat. No. 6,357,304, having a filing date of Sep. 28, 1998, which is a continuation in part of U.S. patent application Ser. No. 08/701,406, now U.S. Pat. No. 5,841,036, filed Aug. 22, 1996.

TECHNICAL FIELD OF THE INVENTION

The present invention relates to spot fluid sampling systems. First disclosed is a "moveable end" (ME) fluid sampling system, which employs a method of collection wherein the initial cylinder volume of the collection vessel or sampling cylinder is zero. In this embodiment, a spot sample cylinder is inserted into the pressurized fluid source, said sample cylinder employing a piston or moveable end to configured to initially be situated in a position wherein the sample cavity has no volume so as to dispense with the necessity of purging same, the moveable end formed to reposition as the sample cavity is filled, thereby expanding the cavity upon sampling.

The present invention also relates to a new and unique cap/body (CB) sample cylinder system having a size and design to enable it to be inserted into a pressurized process with an insertion device. In the preferred embodiment of the CB sample system, the cap functions as a fill/empty valve. The cap and body of the cylinder are designed to eliminate the necessity of purging the sample pathway. The sample cylinder's internal cavity it may be evacuated by pulling a deep vacuum and/or filling with a diluent gas that cannot be detected by the analyzer which will analyze the sampled fluid.

The CB cap to body seal does not require the normally employed sealing materials such as elastomers or plastics. In the preferred embodiment, the cap and body are preferably constructed of metal, and when assembled are formed to provide a metal to metal seal to retain pressurized fluids in the internal cavity of the sample cylinder. A unique housing and method for evacuating the sample gas from the CB sample cylinder is also provided.

BACKGROUND OF THE INVENTION

In many cases, the cost of installing an "on line" analyzer for a natural gas or other process stream cannot be justified. In such cases, a "spot" sample is taken periodically, or a composite sample is taken over a period of time. A "spot sample" generally consists of extracting a sample of the gas at a "spot", or single point in time.

A composite sample is generally taken by a sampling apparatus (composite sampler) which extracts a small volume (bite) of gas sample periodically, which is collected in a sample cylinder. A typical composite sampler will control the sampling interval based on time or flow volume. Flow volume information, or electric pulse, is usually provided by an external flow computer. A typical composite collection period is 30 days. There are two basic types of sample cylinders utilized for spot and composite sampling. They are the constant volume and constant pressure types of sample cylinder. Constant pressure types of sample cylinders are of the floating piston or bladder (bag) type.

Gas Processors Association Standard Publication 2166 entitled "Obtaining natural Gas Samples for Analysis by Gas Chromatography" details several spot sampling methods in its 1986 revision and its draft. The main thrust of the GPA 2166 standard deals with methods for purging the sample cylinder, dealing with entrained liquid using the GPA or other type separator, and prevention of condensation of gas components.

American Petroleum Institute Manual of Petroleum Measurement Standards, Chapter 14, Section 1, revised in 2001, the contents of which are incorporated herein by reference, addresses spot sampling issues.

The hydrocarbon dew point temperature (HCDPT) and its impact on the sampling of natural gas is the main focus of the API 14.1 standard. This is evident in the opening paragraph "14.1 introduction". Refer to 14.1.6, here the standard calls out issues which need to be addressed when sampling natural gas. Issues include ambient temperature condition and phase-change characteristics. In 14.1.6.6, it makes clear that no part of the spot sampling system should be allowed to fall below the HCDPT, otherwise biased analytical results and non-representative samples are likely to result. Maintaining the sample system at, or above, the HCDPT is recommended.

In 14.1.6.6.4 (Sample containers), it states that the cylinder temperature must be kept above the HCDPT. Note that the author is a member of the API 14.1 working group responsible for the writing standard. The reason for this recommendation is to insure that the cylinder temperature is "above" as opposed to "equal" to or above" the HCDPT due to the uncertainty of measuring the HCDPT. It is well known, from a thermodynamic standpoint, that maintaining a gas at or above the HCDPT will not yield condensation.

REFERENCES

1. Gas Processors Association (GPA) standard 2166-1986 and draft copy of 2166-2004 2. API-manual of Petroleum measurement standards chapter 14, section 1, collecting and handling of natural gas samples for custody transfer. API-14.1 revision 2001 3. Southwest research Institute (SRI) San Antonio, Tex. 4 Accuracy of Natural Gas Sampling Techniques, and the impact of composition measurement errors on Flow Rate and Heating value determination. By K. A. Behring II, Southwest research Institute. Paper presented at Flomeko '98, International conference on flow Measurement, (Lund, Sweden, Jun. 15-17, 1998)

The entire API 14.1-2004 document is rich in thermodynamic and practical information. For example, in Appendix A, "The Phase Diagram" and A.1 phase changes in general. In referring to the API 14.1-2004 document, especially its Appendix A and to the paper "Accuracy of Natural Gas Sampling Techniques, and the Impact of Composition Measurement Errors on Flow Rate and Heating Value Determination", K. A. Behring, Flomeko '98, the 9th Int Conf on Flow Measurement, Lund, Sweden (Jun. 15-17, 1998), one can conclude that condensation of portion of a gas phase and/or vaporization of a liquid wherein the resulting vapor becomes intermixed with the gas phase will likely (almost certainly) result in product composition changes in the gas phase.

It is well known and understood that even small changes in the composition of a natural gas sample can have a significant impact on its heating value (BTU content) and other important physical properties some of which are utilized for making flow rate calculations. The heating value and flow rate (volume) of the natural gas key factors in determining its monetary value.

In summary, the cost of adhering to the API 14.1 and GPA 2166 standards, in particular the cost and attention required to maintain all parts of the prior art sampling system and cylinders above the HCDPT, results in the very frequent improper sampling of natural gas. Again, even small changes made to the current and prior art sampling procedures often result in inaccurate, non-representative samples.

The problems are primarily due to the current art of having the sample conditioning system and the sample containment cylinders external to the vessel or pipeline. Spot and composite sample have traditionally been taken in that manner ever since spot samples were first taken. This requires the use of costly equipment, especially in cold climates and/or wet gas (high HCDPT) applications.

General Summary Discussion of the Invention

The present invention overcomes the expense and reliability problems associated with prior art spot sampling techniques in the above scenarios by inserting the sample cylinder of the present invention inside of the pressurized containment vessel or pipeline when taking a sample.

In the first embodiment of the present invention (FIGS. 1A-1B), a spot sample cylinder is inserted into the pressurized gas (or fluid) source, said sample cylinder referenced as an M.E. sample cylinder, as it has a movable end (M.E.) which allows the volume of the cylinder to be dynamically adjustable. This approach does not require the purging or evacuation of the cylinder sample cavity, where the sample cavity volume is essentially zero by virtue of the positioning of the M.E.

A "zero volume sample cavity" such as the M.E. sample cylinder (or any other zero volume sample cavity configuration) can eliminate the need for purging the cylinder. This is important as cylinder purging represents one of the largest and most frequent sources of analytical error in the sampling of natural gas.

Figure 2A:
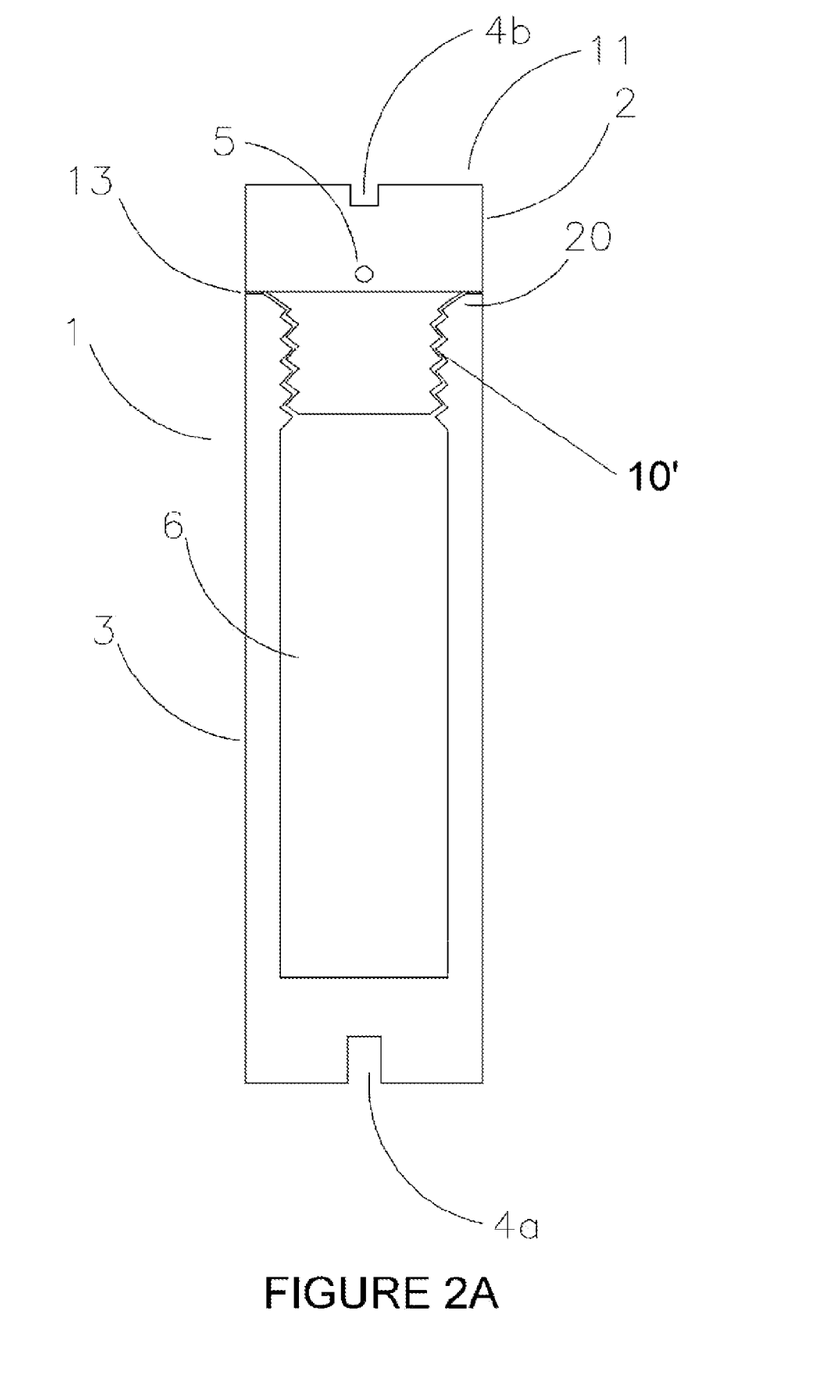
FIG. 2A is a side, partially cut-away, partially cross sectional view of the cap/body (CB) sample cylinder embodiment of the invention configured for evacuation to zero volume prior to sampling via placement into the fluid process (at prevailing pressure and temperature of the fluid stream), or alternatively filled with a residual gas not which would not interfere with the analysis of the fluid stream being sampled prior to sampling, with a cap shown in the closed, sealed position.

To further enhance the sampling system of the present invention, a second embodiment of the invention (ex. FIG. 2A) is provided which contemplates a new and unique cap/body (CB) sample cylinder which is evacuated via a specially designed housing prior to the sampling, such that the initial cylinder volume of the sampling cylinder (or other collection container) is made effectively zero, thereby eliminating the requirement of using prior art cylinder purging techniques which may be prone to altering the sample fluid composition.

An alternative to fully evacuating the CB sample cylinder is to purge said cylinder before sample collection with a diluent gas, such as helium, which cannot be detected by the sample fluid analyzer.

Still another technique of the present invention is to first purge the CB sample cylinder with a diluent gas which cannot be detected by the sample fluid analyzer, followed by reducing the diluent gas pressure in the cylinder to essentially zero by evacuation.

In each of the above cases, the cap is sealed to the CB sample cylinder body after purging and/or evacuation of the internal cylinders cavity, preferably while utilizing a custom housing for that purpose, also disclosed in the present application.

Insertion of either sample cylinder directly into the process source of fluid for the sample eliminates the requirement for purging any tubing/piping interconnection(s) between the process and sample cylinder, when traditional external filling method is utilized.

Purging of the interconnecting tubing/piping and sample cylinder is the greatest source of error in spot sampling. The present invention eliminates this source of error. The present invention can also be filled external to the source fluid. Due to its design, the sample path from the source of fluid to the cylinder is minimized, thereby limiting the exposure to ambient temperature during the sampling process.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein.

DETAILED DISCUSSION OF THE INVENTION

Figure 1A:
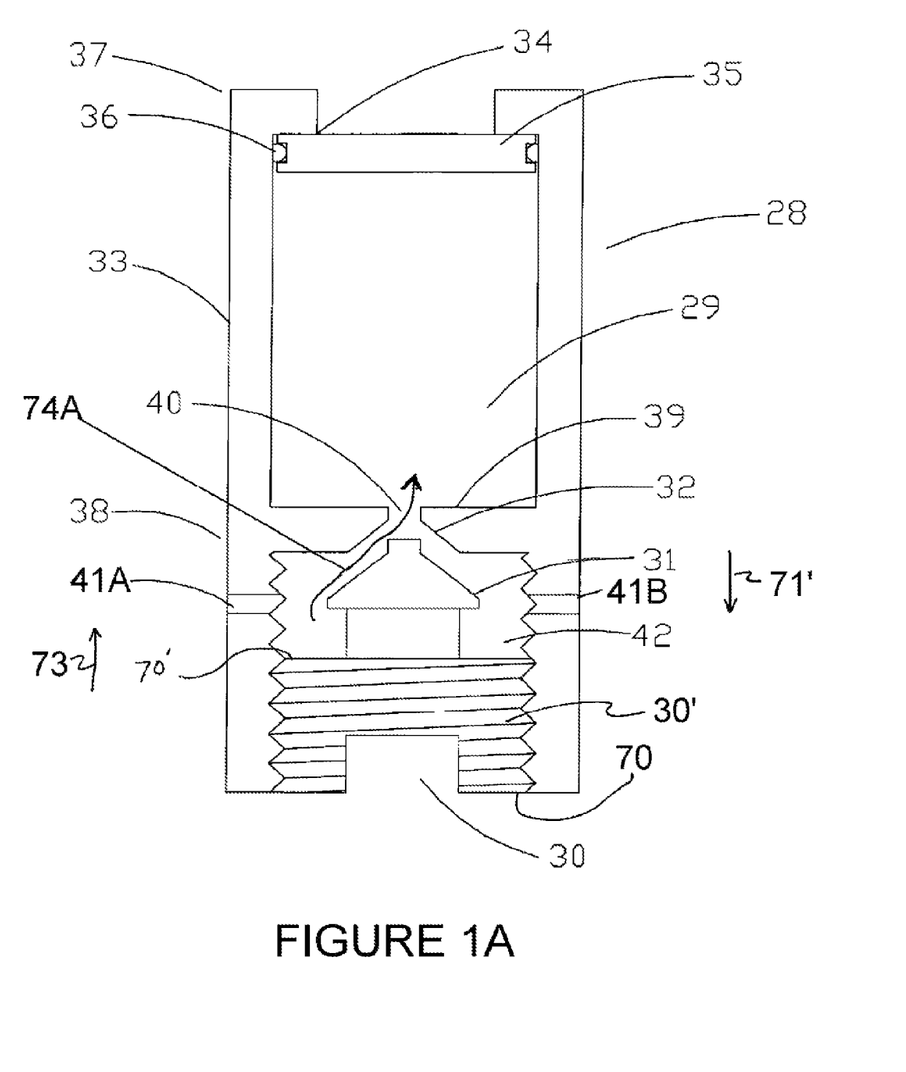
FIG. 1A is a side, a partially cut-away, partially cross-sectional view of an exemplary design for a sample cylinder having a moveable end (M.E. Sample Cylinder) for use in the present invention, wherein the moveable end is shown at the first end of the sample cavity.
Figure 1B:
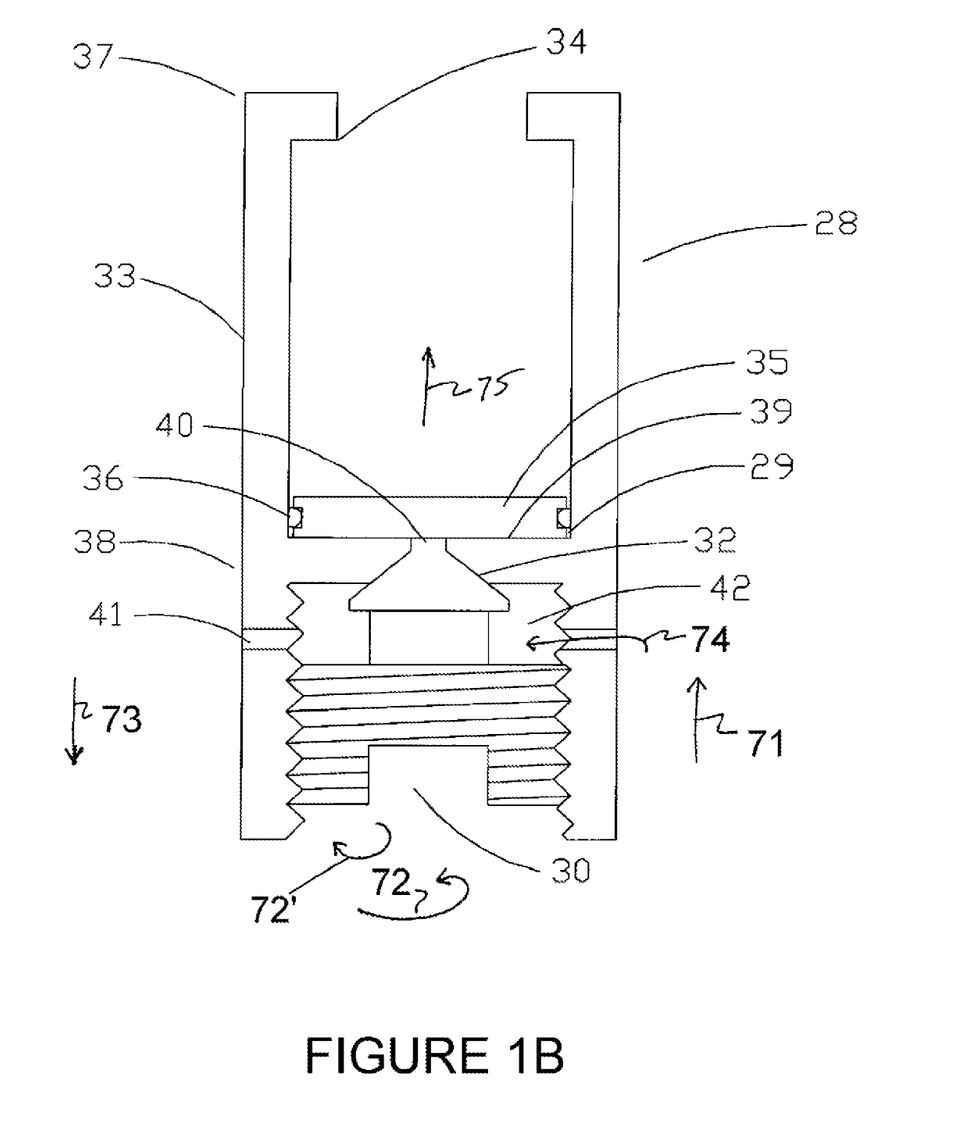
FIG. 1B is a side, partially cut-away, partially cross-sectional view of the device of FIG. 1A, wherein the moveable end is shown at the second end of the sample cavity.

The first embodiment of the sample cylinder of the present invention is shown in FIGS. 1A and 1B. The moveable end (ME) sample cylinder 28 is comprised of a cylinder wall 33, having a mechanical end stop 34 at a first end 37, valve seat 32 at a second end 38, valve stem/poppet 31 mounted to threaded plug 30', movable end 35, seal 36, Hex recess 30, sample cavity 29, and valve 40 formed by valve stem/poppet 31 and valve seat 32 situated in valve chamber 42. Fluid flow passages 41A, 41B allow fluid from into valve chamber 42.

As shown, moveable end 35 slidingly engages the inner wall of sample cavity 29 to form a sliding barrier which is fluid sealed or fluid impermeable via seal 36, which can comprise, for example, an o-ring. In the exemplary embodiment, valve chamber 42 has an inner wall forming a threaded connection for threadingly engaging threaded plug 30' having first 70 and second 70' ends, the first end 70 having hex recess 30 formed therein, the second end 70' having valve stem/poppet 31 engaged thereto.

As shown in FIG. 1A, moveable end 35 is at first end 37 against mechanical stop 34 and valve stem/poppet 31 is retracted from valve seat 32. In this position, sample cavity 29 is at its maximum volume and valve 40 is opened.

In FIG. 1B, moveable end 35 is at second end 38 against mechanical stop 39 and valve 40 is in the closed position, wherein the stem/poppet 31 is seated to valve seat 32. In this position, sample cavity 29 is at its minimum volume or essentially zero volume. Thus, the sample cavity provides a variable volume dependent upon the location of the mechanical stop relative to the first 37 and second 38 ends.

This moveable end (ME) sample cylinder may be inserted into a pressurized fluid source for obtaining a sample by a number of means. One such means utilizes a packing gland or dynamic pressure seal type of insertion device, similar to that used for insertion of probes, sensors, corrosion coupons etc. A second type of insertion means to insert the ME sample cylinder into a pressurized process utilizes a pressure balance approach similar to that described in U.S. Pat. No. 7,472,615 by Mayeaux entitled "Portable Insertable Probe assembly", the contents of which are incorporated herein by reference.

Referring to FIGS. 1A and 1B, with the moveable end 35 at the minimal volume position (as in FIG. 1B), with the valve closed, the sample cylinder is inserted 71 into a pressurized fluid source for sampling. Threaded plug 30' may then be turned 72 in a first direction via hex recess 30 to open 73 valve 40 (as in FIG. 1A), so as to allow fluid from the pressurized fluid source to migrate through 74 passages 41A, 41 B into valve chamber 42, through the open 73 valve, and into 74 A sample cavity 29, where moveable end 35 (FIG. 1B) is slidingly urged 75 from the second end 38 to the first end 37 via pressure from the fluid entering the sample cavity 29, filling sample cavity with fluid, as movable end 35 migrates to the first end 37.

Once the sample cavity has reached the first end 37, and is thereby filled, the threaded plug 30 may be turned 72' a second direction via hex recess 30 to close 73' valve 40, capturing and retaining the fluid in the sample cavity, thereby providing a filled sample cylinder, which may be then removed 71' from the pressurized fluid source for analysis or other purpose.

With the ME sample cylinder inserted into the pressurized fluid source, the above sample has been taken at prevailing temperature and pressure, providing an accurate sample of the contents of the pressurized fluid source.

A method of using the ME sample cylinder of the present invention may thereby be summarized as follows:
a. providing a spot sample container, comprising:
   a housing having formed therein a sample cavity having first and second ends, and a wall;
   a moveable end slidingly engaging said wall of said sample cavity, so as to form a moveable fluid barrier within said sample cavity, having a variable volume associated with the position of said moveable barrier;
   a valve associated with said sample cavity;
b. immersing said container into a pressurized fluid process;
c. allowing the temperature of said container to adjust to the temperature of said pressurized fluid process;
d. opening said valve;
e. allowing fluid from said pressurized fluid process to migrate into said sample cavity;
f. allowing said moveable stop to slidingly migrate from said first end of said sample cavity to said second end of said sample cavity as said sample cavity fills with fluid;
g. closing said valve, providing a filled spot sample container; and
h. removing said filled spot sample container from said pressurized fluid process.

As an alternative to the zero volume methodology, above, a sample cylinder or other sample container may be evacuated prior to use to insure non-contamination of the sample cavity. Unlike the zero volume methodology above, evacuation of the sample cylinder prior to the sampling process eliminates the necessity of a moveable fluid barrier to selectively provide zero volume in the exemplary method illustrated in steps a-h, above. An alternative to evacuation could comprise the utilization of an inert gas, such as helium or the like, which could be provided at a pressure less than the process fluid to prevent contamination prior to sampling.

Figure 2B:
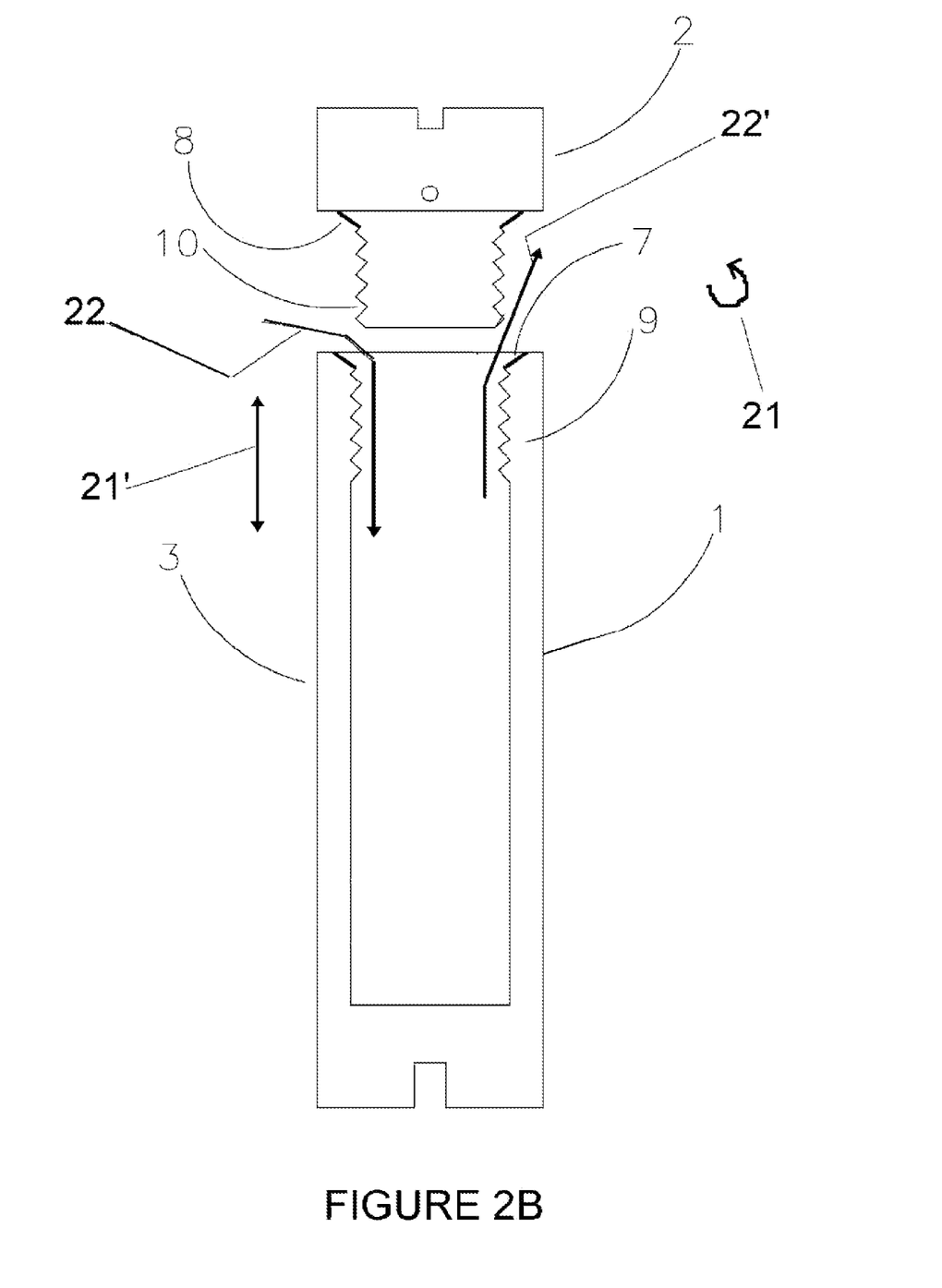
FIG. 2B is a side, partially cut-away, partially cross-sectional view of the CB sample cylinder of FIG. 2A, illustrating the cap separated from the body and showing the positions of the cap sealing surface (7) and body sealing surface (8).
Figure 3:
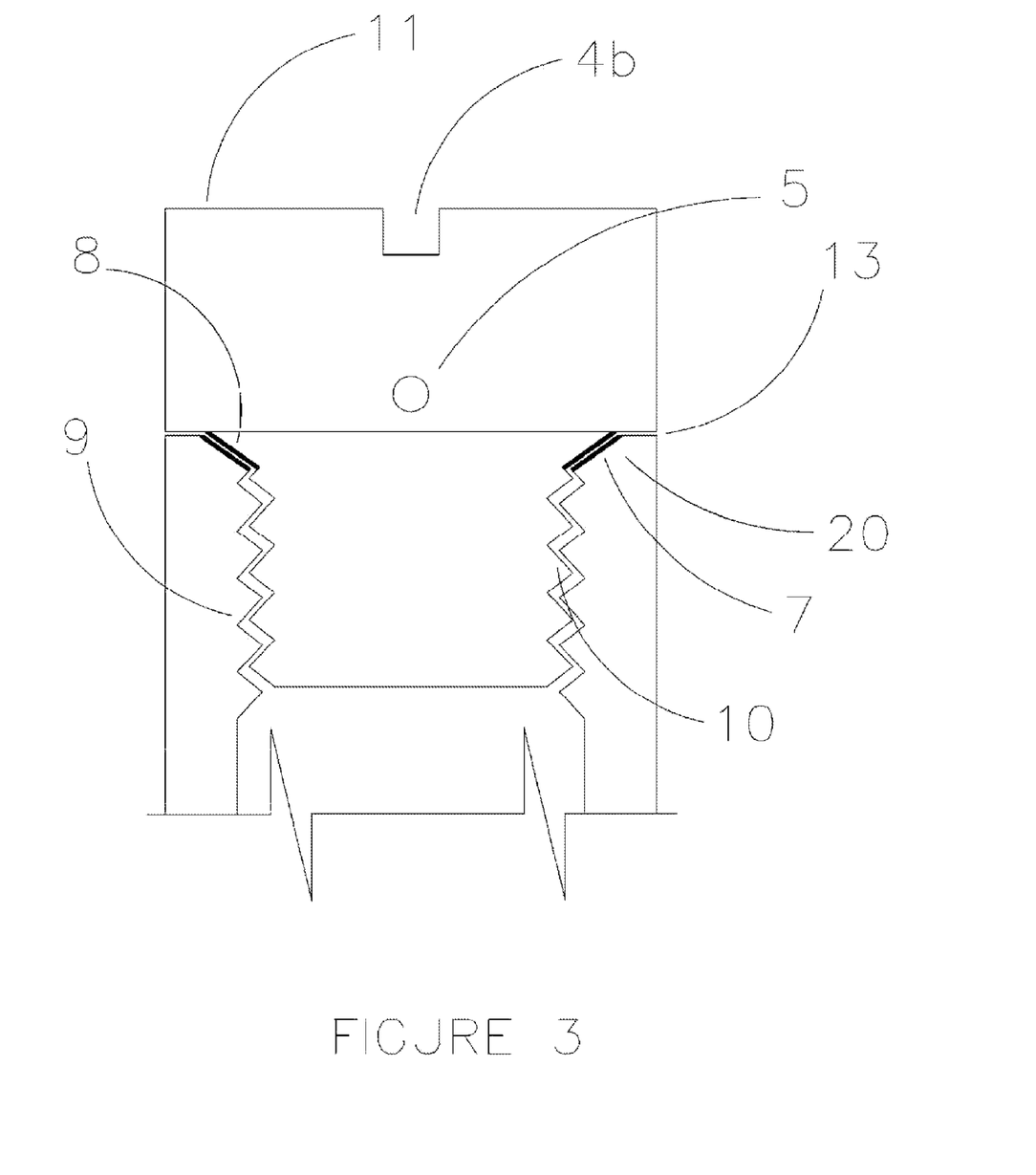
FIG. 3 is a partial, close-up, side, partially cut-away, partially cross-sectional view of the CB sample cylinder of FIG. 2A, illustrating the cap engaging the body in a closed, sealed position, illustrating the threaded engagement therein, as well as engagement of the cap sealing surface (7) to the body sealing surface (8).

The present concept of spot sampling using a pre-evacuated sample cylinder is detailed in FIGS. 2A-6B. FIGS. 2A, 2B and 3 provide an overview of the contemplated sample cylinder (referenced as cap/body (CB) sample cylinder), and are referenced in the following discussion. The CB sample cylinder 1 is comprised of a cap 2 and a body 3. When cap threads 10 are threadly engaged 10' fully to body threads 9, the cap seal 8 surface and body seal 7 surface engage to form a closed valve 20, so as to isolate cavity 6 from ambient and form a container for any fluids therein.

By loosening 21 the cap from the body via turning the cap or body so as to loosen the threaded engagement 10' between cap threads 10 and body threads 9, body seal 7 surface and cap seal 8 surface are separated 21' from one another other, forming a space therebetween to allow fluid passage into 22 and out 22' of cavity 6 via a fluid pathway which passes between separated body seal 7 surface and cap seal 8 surface, as well as the space forming the groove 13 between the body and cap. Body and cap threads 9, 10, respectively, in the present embodiment preferably have a tolerance relative one another so as to facilitate the passage of pressurized fluid therebetween when loosened so that the cap need not be fully removed from the body for the passage to occur, with fluid passage preferably possible upon separation of the cap seal 8 from the body seal 7.

Continuing with FIGS. 2A, 2B and 3-5, a uniquely configured housing 14A is provided for evacuating the sample cylinders, as well as collecting the sample therefrom. Housing 14A has a side wall 80 forming a longitudinally oriented receiver 80' having inner surface 82 forming an inner diameter 81, the receiver 80' formed to receive the outer diameter 81' of CB sample cylinder 1 and cap 2, with the inner surface 82 of the receiver 80' in housing 14A, (preferably) effectively enveloping the length 83 of the sample cylinder. This allows the housing (by way of the receiver) to be used to isolate the junction of cap 8 and body 7 at groove 13, via O-rings 15A, 15B situated on opposing sides of groove 13, the O-rings spanning the ID 81 of receiver 80' and the OD 81' of sample cylinder, sealing same so as to form a containment zone 13' between said O-Rings 15A, 15B, containing the area to direct the passage of fluids into 22 or out of 22' sample cavity 6 via port 18.

Figure 4:
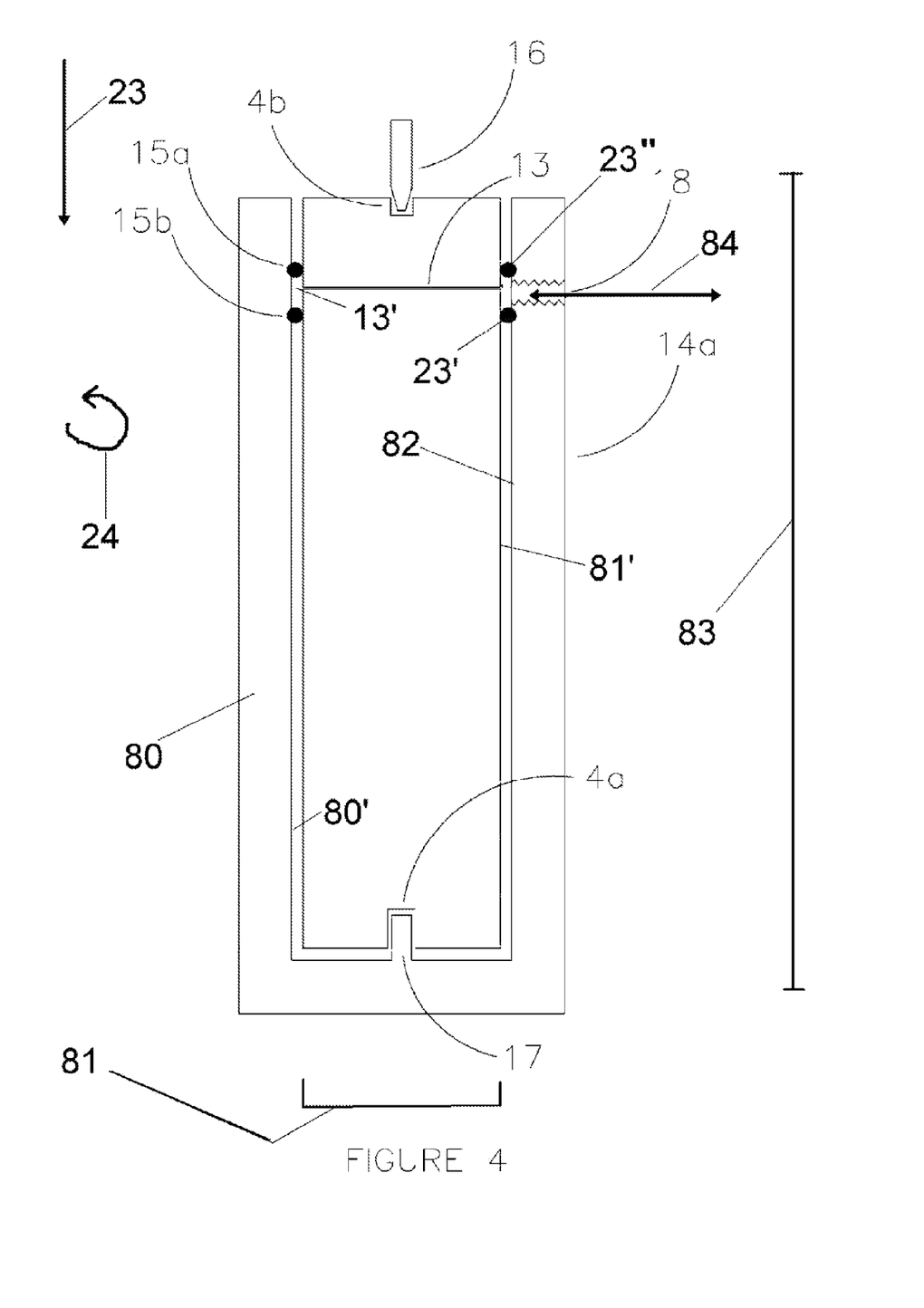
FIG. 4 illustrates the sample cylinder of FIG. 2A engaged to housing 14A, with sealing O rings (15a and 15b) situated juxtaposed either side of the engagement of the CB sample cylinder cap and body formed so as to allow the evacuation of the volume of the sample cylinder, as will be further explained herein.
Figure 5:
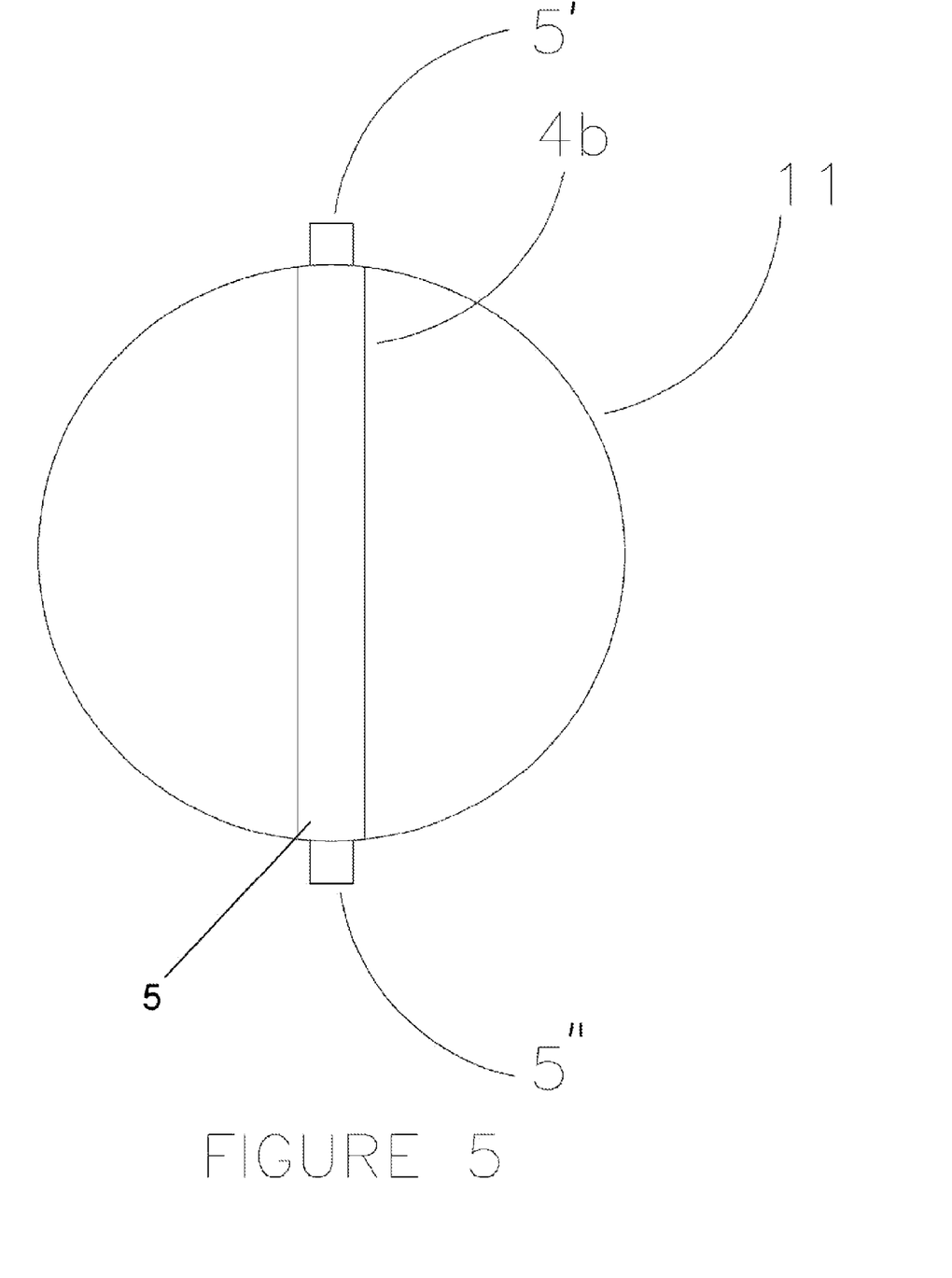
FIG. 5 is a top view of the cap of FIG. 2A illustrating the position of an slot formed on its upper surface, and pins longitudinally aligned therewith, and emanating from the diameter therefrom.
Figure 6:
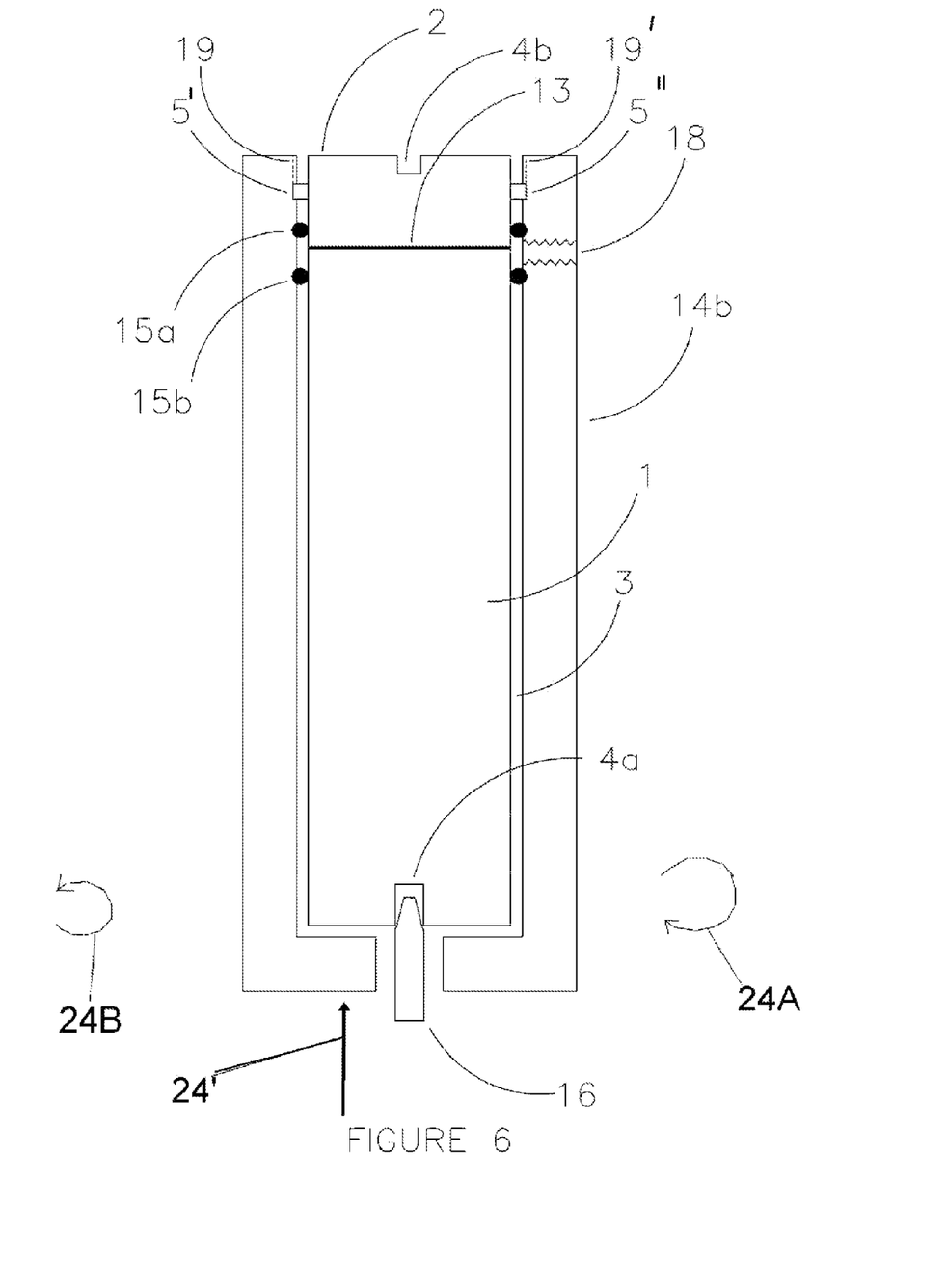
FIG. 6 illustrates a side, cut-away view of the invention of FIG. 2A, wherein the pins of FIG. 5 are situated in slits formed in the housing as the body and cap forming the CB sample cylinder are placed in the housing, so as to lock the cap in position so that the body of the cylinder can be rotated along its axis (such as with a screwdriver or the like) to unseal the cap from the body and allow the evacuation of the volume of the sample cylinder via passage 18.
Figure 6A:
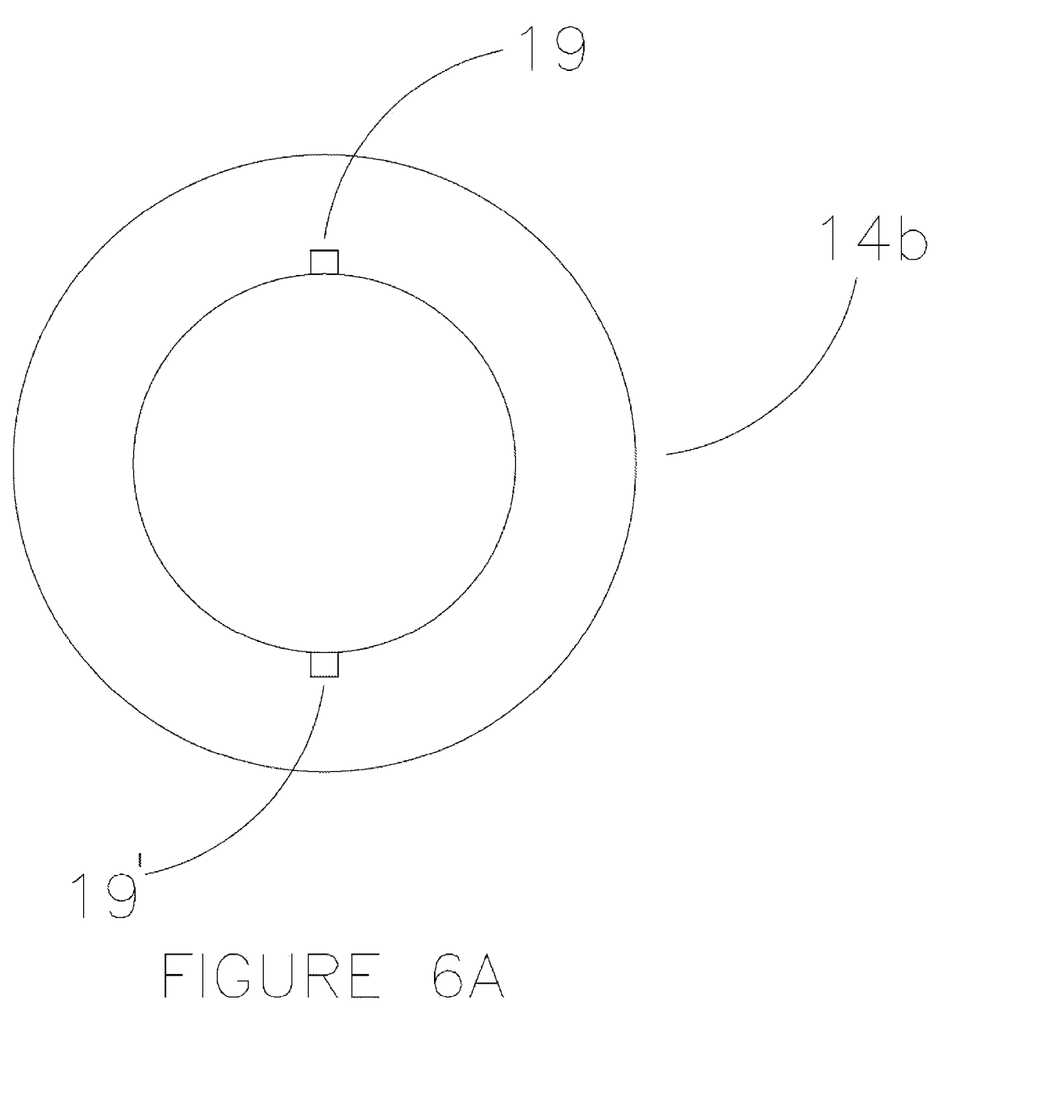
FIG. 6A is a top view of the housing of FIG. 6, illustrating the pin slots 19, 19' formed therein.
Figure 6B:
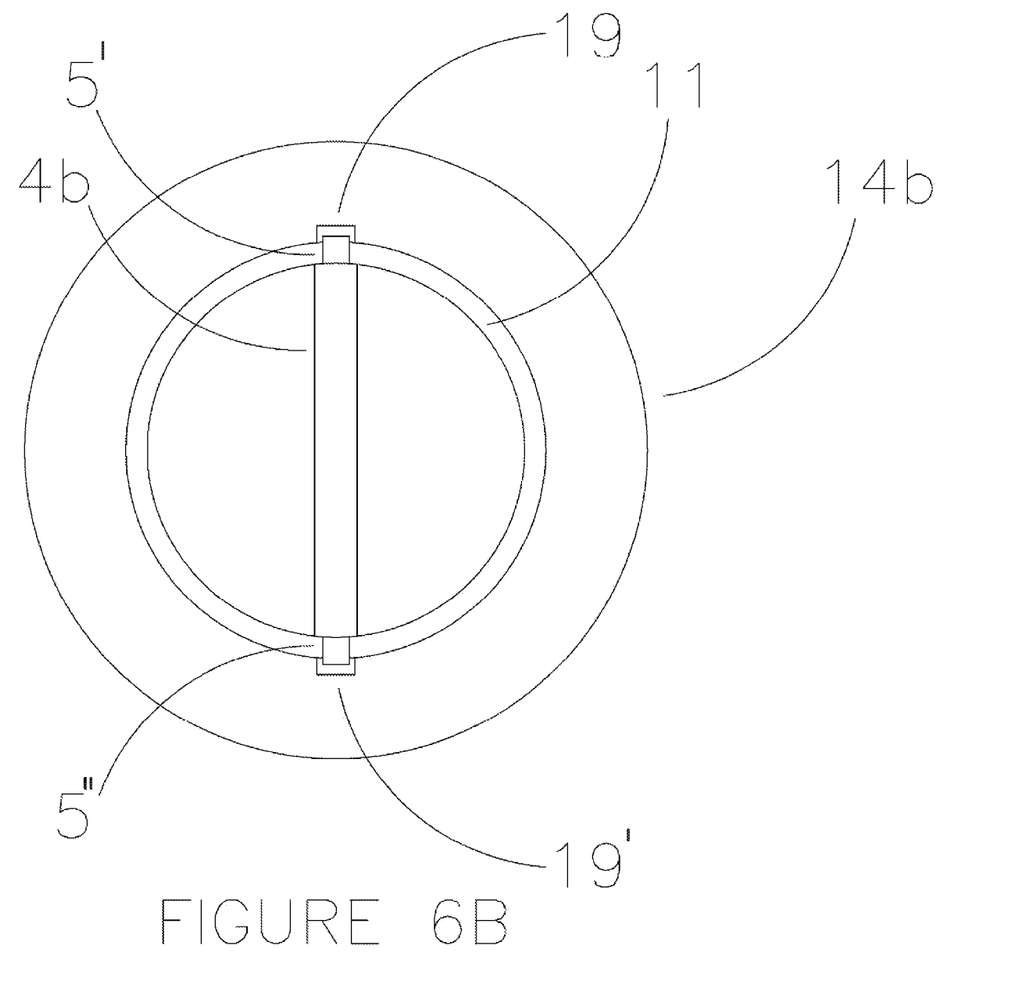
FIG. 6B is a cross-sectional view of the top of the housing of FIG. 6.

When CB sample cylinder is inserted 23 into housing 14a, FIG. 4, slot 4a is engaged with stationary flat blade 17 and groove 13 is isolated from the ambient via seals 23', 23" formed by opposing O rings 15a and 15b, each engaging inner surface 82 of housing and outer surface 81" of CB sample cylinder, respectively, so as to allow cavity 6 to be evacuated, or filled with diluting, non-detectable gas, or emptied of its contained sample via threaded port 18, when cap threads 10 and body threads 9 are loosened 24 by use of a flat bladed screwdriver 16 engaged with slot 4b, so as to separate cap seal 8 from body seal 7, to allow the passage 84 of fluid therebetween.

It is noted here that the term "sampling cylinder" or "micro cylinder" is not intended to limit the structure to sampling, or containers which may be used for other purposes, such as collection and storage. Accordingly, the terms "sampling cylinder", "micro cylinder" or the like should be considered in the present disclosure as synonymous with storage cylinder, collection cylinder, or like devices.

During sampling, one inserts the CB sample cylinder into the fluid process and loosens the cap 2 from the body 3 so as to separate the body seal 7 from the cap seal 8, so as to allow the passage of the sample to pass directly into 22 the sample cylinder, at which point the cap 2 is tightened upon the body 1, causing the body seal 7 and cap seal 8 to engage, thereby containing the sample situated therein.

After the sample is collected, the CB sample cylinder is placed into the housing 14a, the cap 2 is loosened from the body 3, again separating the body seal 7 from the cap seal 8, allowing the passage of the sample from the sample cylinder, and through threaded port 18 for analysis, storage, further processing, etc.

The CB sample cylinder, having no contaminates in its sample cavity by virtue of lowering the pressure to essentially zero or having residual gas which cannot be detected by the sample fluid analyzer, at the beginning of a sampling procedure, and eliminating liquids and particles from the sample gas entering the sample cylinder, the three largest sources of error in spot sampling are eliminated.

Again, preventing vapor/liquid equilibrium changes (which alter the gas phase composition) is accomplished by sampling at the prevailing source fluid conditions of pressure and temperature, since the cylinder is immersed "in" the fluid source.

By providing a phase separation membrane during sampling, and allowing the sample gas to flow through a phase separation membrane designed to reject liquids (all types) and particles before entering the sample cylinder, entrained liquids are eliminated. The separated liquid can either be drained back into the pressurized process, or captured for analysis or the like.

Removing entrained liquids (in the case of gas sources such as natural gas) by using a phase separating membrane, which rejects liquids while allowing gases and vapors to flow through, eliminates the equilibrium changes by sampling only the gas phase of the fluid source at the prevailing pressure temperature conditions of the gas source. Particles are removed with the phase separating membrane and/or any other type suitable particulate filter prior to entry into the sample cylinder.

Having a near zero cylinder volume or undetectable diluent gas in the sample cavity can eliminate the need for purging the cylinder, which said cylinder purging represents one of the largest and most frequent sources of analytical error in the sampling of natural gas. Insertion of the ME or CB sample cylinder into a pressurized fluid process utilizing the dynamic sealing and pressure equalization can be accomplished with sample probes or the like.

Another option for opening and closing the valve formed by body sealing surfaces 7 and cap sealing surface 8 when the sample cylinder is in the housing is accomplished with the alternative design housing 14b, FIGS. 5, 6, and 6A-6B. Pin 5 having opposing ends 5', 5" engaged 24 in pin slots 19, 19", respectively, to prevent cap 2 from rotating within housing 14b.

Flat blade screwdriver 16 engaged 24' in slot 4a permits rotation 24" of the body 3 to facilitate the opening 24A and closing 24B of valve 20 formed by sealing surface 7 and sealing surface 8, respectively. This embodiment is different in that the body is turned relative to the cap, as opposed to the cap being turned relative to the body (shown in the embodiment of FIGS. 2A-5), but otherwise, the method of preparation of the sample cylinder for testing, the testing procedure, and the procedure for removal of the sample from the cylinder is the same as that discussed in the embodiment of housing 14A.

An example of a method of sampling utilizing the apparatus of the present invention may comprise the steps, for example, of:

A. Providing a sample container comprising: A body therein a sample cavity, said body being formed so as to be immersed into a pressurized fluid process, and having threads and a sealing surface, a threaded cap with metal sealing surfaces being formed so as to mate with said threaded section and sealing surface of said body;

B. Inserting said container into a pressurized fluid;

C. Allowing the temperature of said container to reach equilibrium with the temperature of said pressurized fluid;

D. Loosening said threaded cap from said body threads, and allowing fluid from said pressurized process to migrate into said sample cavity;

E. Tightening said threaded cap to said threaded body so as to isolate said sample cavity;

F. Withdrawing said sample container from said pressurized process.

Once again referring to FIGS. 2A-4, the housing 14A (or 14B, FIG. 6) of the present invention may be utilized to prepare the sample cylinder prior to testing by placing the sample cylinder into the receiver, loosening the threads of the cap and body to separate the seals therebetween, so as to allow the flow of fluid therebetween. A vacuum may then be established via port 18 so as to evacuate containment zone 13', and, with the seals 7, 8 separated, fluid in the cavity 6 of sample cylinder flows therefrom due to pressure differential, evacuating same.

Alternatively, but in similar fashion, diluent fluid may be introduced via pressurized flow through port 18 to flow into cavity 6 to urge contaminants from said cavity 6, or a combination of diluent fluid and evacuation may be used. A second port may be provided through sidewall 80 of housing, communicating with said containment zone 13' for egress of diluent fluid in such an operation. Said cap is then tightened to said body so that seals 7, 8 are engaged, the sample cylinder is removed, then the sample is taken.

For example, the sample cylinder may be placed into a fluid to be sampled, where it is allowed to reach the temperature of the fluid, then the cap and/or body of the sample cylinder is loosened to separate seals 7, 8, so that fluid can flow into cavity 6 for sampling, then the cap is tightened to the body to close seals 7, 8, containing the fluid in the cavity for sampling.

The sample cylinder may then be placed into the housing, the cap loosened relative the body (or visa versa) to separate the seals 7, 8, allowing extraction of the fluid therein via containment zone 13' and port 18.

| Elements of the CB sample cylinder: | |
|---|---|
| Element | Description |
| 1 | CB type sample cylinder |
| 2 | Cap |
| 3 | Body |
| 4a | Slot |
| 4b | Slot |
| 5, 5', 5" | Pin, pin ends |
| 6 | Cavity |
| 7 | Body Sealing Surface |
| 8 | Cap Sealing Surface |
| 9 | Body Female Threads |
| 10 | Cap Male Thread, 10' threads engaged |
| 11 | Upper Cap Surface |
| 12 | Flat Surface |
| 13 | Groove between cap and Body |
| 13' | Containment zone |
| 14 | Housing for filling/emptying sample cylinder |
| 15a | O Ring |
| 15b | O Ring |
| 16 | Flat blade screwdriver |
| 17 | Flat blade |
| 18 | Housing Port |
| 19 | Pin Slots |
| 20 | Valve |
| 21 | Loosened, 21' moves away/spaced apart |
| 22 | Sample migration into cavity, 22' out of cavity |
| 23, 23' | Sealed |
| 24 | loosened |
| 80 | side wall of housing |
| 80' | receiver |
| 81, ', " | ID receiver, OD sample cylinder, outer surface |
| 82 | inner surface receiver |
| 83 | length of sample cylinder |

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A device for obtaining a fluid sample, comprising:
   a sample container having an outer diameter, comprising:
      a body having a length forming first and second ends, and a longitudinal axis, said first end being threaded and forming an opening to a sample cavity having inner walls forming an inner diameter, said second end being closed;
      a cap having threaded ends formed to engage said threaded first end of said body;
      said cap and body having first and second seals, respectively, formed to engage one another when said threaded cap and body are tightened, forming a junction therebetween, said first and second seals, when engaged, being formed to prevent the passage of fluid therebetween;
   whereby, upon tightening said threaded cap about said threaded end of said body, said first seal of said cap engages said second seal of said body so as to prevent the passage of fluid therebetween.

2. The device of claim 1, wherein there is further provided a housing comprising:
   a side wall forming a longitudinally oriented receiver having an inner surface forming an inner diameter, the receiver formed to receive said outer diameter of said sample container;
   first and second seals positioned to be situated between said outer diameter of said sample container and said inner diameter of said receiver, said first and second seals situated on opposing sides of said junction formed by the engagement of said tightened cap and body so as to form a containment zone thereabout;
   a passage formed through said side wall of said housing communicating with said containment zone.

3. The device of claim 2, wherein, upon placing said sample container in said housing, said length of said sample container is enveloped by said receiver such that, upon loosening said threaded engagement of said cap with said body of said sample container, said first and second seals of said sample container separate to allow the passage of fluid therebetween, so as to allow the free flow of fluid between said sample cavity within said sample container and said containment zone formed in said receiver of said housing.

4. The device of claim 3, wherein said sample container comprises a sample cylinder.

5. The device of claim 3, wherein said body of said sample container has a longitudinal axis, and wherein said body of said sample cylinder is formed to engage said housing so as to prevent the rotation of said sample container about said axis.

6. The device of claim 5, wherein said cap of said sample cylinder is formed to receive a tool for rotating same while said sample cylinder engaged in said housing, so as to loosen said threaded engagement of said cap from said body.

7. The device of claim 3, wherein said cap of said sample container has a longitudinal axis, and wherein said cap of said sample cylinder is formed to engage said housing so as to prevent the rotation of said cap about said axis.

8. The device of claim 7, wherein said sidewall of said receiver formed in said housing has opposing longitudinally oriented first and second slots formed therein, and wherein said cap has emanating therefrom first and second opposing pins emanating therefrom, said first and second pins formed to engage said first and second slots, respectively, so as to engage said cap to selectively prevent rotation of said cap.

9. The device of claim 8, wherein said second end of said body has a slot formed therein.

10. The device of claim 7, wherein said second end of said body of said sample cylinder is formed so as to receive a tool for rotating same while said cap is engaged in said housing, so as to loosen said threaded engagement of said body from said cap.

\* \* \* \* \*